(12) United States Patent
Helmlinger et al.

(10) Patent No.: US 6,368,858 B1
(45) Date of Patent: *Apr. 9, 2002

(54) MODULATION OF MULTICELLULAR AGGREGATES BY PRESSURE FROM GROWTH IN A MATRIX

(75) Inventors: Gabriel Helmlinger, Brussels (BE); Paolo A. Netti, Naples (IT); Robert J. Melder, Gaithersburg, MD (US); Rakesh K. Jain, Boston, MA (US); Hera Lichtenbeld-Dubois, Maastricht (NL)

(73) Assignee: The General Hospital Corporation, Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/120,136

(22) Filed: Jul. 22, 1998

Related U.S. Application Data

(60) Provisional application No. 60/053,409, filed on Jul. 22, 1997.

(51) Int. Cl.$^7$ ............................. C12N 5/06; C12N 5/08; C12N 11/02; C12N 11/10; C12N 11/04
(52) U.S. Cl. ...................... 435/382; 424/93.7; 424/423; 435/177; 435/178; 435/182; 435/395
(58) Field of Search ................................ 435/177, 178, 435/382, 395; 424/93.7, 423

(56) References Cited

U.S. PATENT DOCUMENTS

| | | | |
|---|---|---|---|
| 4,680,174 A | | 7/1987 | Jarvis, Jr. et al. .............. 424/85 |
| 5,643,569 A | | 7/1997 | Jain et al. .................... 424/93.7 |
| 5,800,828 A | * | 9/1998 | Dionne et al. ............... 424/422 |
| 5,888,497 A | * | 3/1999 | Jain et al. ................... 424/93.7 |
| 5,980,889 A | * | 11/1999 | Butler et al. ................ 424/93.7 |

OTHER PUBLICATIONS

Helmlinger et al., "The Solid Stress–Induced Growth Inhibition of Tumor Spheroids is Accompanied by an Increased Cellular Density and Reduced Apoptotic Rate", Abstract No. P28–539, 45$^{th}$ Annual Meeting of the Radiation Research Society, Providence, RI, May 1997.
Helmlinger et al., "Inhibition of Tumor Growth by Solid Stress," Abstract No. F217, 9$^{th}$ International Congress of Biorheology, Big Sky, MT, Jul. 1995.
Helmlinger et al., "Growth Inhibition of Tumor Spheroids by Solid Stress," Abstract No. 251, 9$^{th}$ NCI–EORTC Symposium on New Drugs in Cancer Therapy, Amsterdam, The Netherlands, Mar. 1996.
Gompertz; "The nature of the function expressive of the law of human mortality, and on a new mode of determining the value of Life Contingencies"; Phil. Trans. R. Soc. 115:513–585 (1825).
Fung; "Biomechanical Aspects of Growth and Tissue Engineering"; Biomechanics, Motion, Flow Stress and Growth, (ed. Fung, Y.C.), 499–546 (1990).
Y.C. Fung et al.; "Change of Residual Strains in Arteries due to Hypertrophy Caused by Aortic Constriction"; Circulation Research vol. 65, No. 5, pp. 1340–1349 (1989).
Y.C. Fung; "What Are the Residual Stresses Doing in Our Blood Vessels?"; Annals of Biomedical Engineering, vol. 19, pp. 237–249 (1991).
Vaage; "Fibrosis in Immune Control of Mammary–Tumor Growth"; Int. J. Cancer vol. 51, pp. 325–328 (1992).
Gartner et al.; "Unusual growth characteristics of human melanoma xenografts in the nude mouse: a model for desmoplasia, dormancy and progression"; British Journal of Cancer vol. 65, No. 4, pp. 487–490 (1992).
Eaves., "The invasive growth of malignant tumours as a purely mechanical process"; The Journal of Pathology vol. 109, No. 3; pp. 233–237 (1973).
Young; The invasive growth of malignant tumours: an experimental interpretation based on elastic–jelly models; The Journal of Pathology and Bacteriology vol. 77, No. 2; pp. 321–339 (1959).
Falk; "Patterns of Vasculature in Two Pairs of Related Fibosarcomas in the Rat and their Relation to Tumour Responses to Single Large Doses of Radiation"; Europ. J. Cancer vol. 14, pp. 237–250 (1978).
Falk; "The Vascular Pattern of the Spontaneous C3H Mouse Mammary Carcinoma and its Significance in Radiation Response and in Hyperthermia"; Europ. J. Cancer vol. 16, pp. 203–217 (1980).
Tozer et al.; "The relationship between regional variations in blood flow and histology in a transplanted rat fibrosarcoma"; British Journal of Cancer vol. 61, No. 2, pp. 250–257 (1990).
Li et al.; "Correlation of Growth Capacity of Human Tumor Cells in Hard Agarose With Their In Vivo Proliferative . . . Metastatic Sites"; Journal of the National Cancer Institute vol. 81, pp. 1406–1412 (1989).
Jain; "Determinants of Tumor Blood Flow: A Review"; Cancer Research vol. 48, No. 10, pp. 2635–2944 (1988).
Knight et al.; "Distribution of chondrocyte deformation in compressed agarose gel using confocal microscopy"; Cellular Engineering 1, pp. 97–102 (1996).

(List continued on next page.)

Primary Examiner—David M. Naff
(74) Attorney, Agent, or Firm—Fish & Richardson P.C.

(57) ABSTRACT

Cells in a matrix or in the matrix in a vessel are grown to form a multicellular aggregate. Pressure is exerted on the growing cells by the matrix or the matrix together with the vessel due to growing cellular mass displacing the matrix. A value representing pressure exerted on the cells is calculated and the pressure is modulated to control growth of the multicellular aggregate, or to produce a multicellular aggregate of a pre-selected size or a pre-selected size and shape. Matrices include agarose, alginate and collagen gels, and the pressure exerted on the cells can be non-isotropic. The cells may be tumor cells, or liver, pancreatic, brain, skin, bone or muscle cells, and cell growth can be in vitro or in vivo. When collagen forms the matrix, the matrix may contain glycosaminoglycan.

27 Claims, 4 Drawing Sheets

OTHER PUBLICATIONS

Sutherland; "Cell and Environment Interactions in Tumor Microregions: The Multicell Spheroid Model"; Science 240, pp. 177–184 (1988).

Freyer; "Role of Necrosis in Regulating the Growth Saturation of Multicellular Spheroids"; Cancer Research vol. 48, No. 9, pp. 2432–2439 (1988).

Nicolson et al; "Growth of Rat Mammary Adenocarcinoma Cells in Semisolid Clonogenic Medium . . . from Different Sized Colonies"; Cancer Research vol. 48, No. 2, pp. 399–404 (1988).

Boucher et al.; "Microvascular Pressure Is the Principal Driving Force for Interstitial Hypertension in Solid Tumors: Implications for Vascular Collapse"; Cancer Research 52, 5110–5114, (1992).

Boucher et al.; "Interstitial Pressure Gradients in Tissue–isolated and Subcutaneous Tumors: Implications for Therapy"; Cancer Research vol. 50, No. 15, pp. 4478–4484 (1990).

Boucher et al.; "Tumor Angiogenesis and Interstitial Hypertension"; Cancer Research vol. 56, No. 18, pp. 4264–4266 (1996).

Netti et al.; "Effect of Transvascular Fluid Exchange on Pressure–Flow Relationship in Tumors: A Proposed Mechanism . . . Tumor Blood Flow Heterogeneity"; Microvascular Research 52, Article No. 0041, pp. 27–46 (1996).

Iscove et al.; "Clonal Growth of Cells in Semisolid or Viscous Medium"; Immunological Methods; pp. 379–385 (1979).

C.B. Jaeger et al.; "Polymer encapsulated dopaminergic cell lines as "alternative neural grafts""; Progress in Brain Research, vol. 82:41–46; (1990).

C.B. Jaeger et al.; "Growth of tumour cell lines in polymer capsules: ultrastructure of encapsulated PC12 cells"; Journal of Neurocytology, vol. 21:469–480 (1992).

S. Darquy et al.; "Immonoisolation of pancreatic B cells by microencapsulation"; Diabetologia vol. 28:776–780 (1985).

* cited by examiner

MODULATION OF MULTICELLULAR AGGREGATES BY PRESSURE FROM GROWTH IN A MATRIX

CROSS-REFERENCE TO RELATED APPLICATION

This application claims priority under 35 U.S.C. §119 from U.S. Ser. No. 60/053,409, filed Jul. 22, 1997.

STATEMENT AS TO FEDERALLY SPONSORED RESEARCH

This invention was made, at least in part, with funds from the Federal Government, awarded through the National Cancer Institute under contract R35-CA-56591. The government therefore has certain rights in the invention.

BACKGROUND OF THE INVENTION

This invention relates to modulating the growth of multicellular aggregates (e.g., tumors).

In tissue engineering, the successful development of a cell-based implant for restoring or improving body function through the production and/or secretion of bioactive substances is dependent upon the growth state and spatial organization of cells within the implant. For example, hepatocytes that are cultured in vitro in a three-dimensional configuration retain a more differentiated state and display more liver-specific functions than do cells grown in a two dimensional system. Similarly, the control of growth rates is of importance in biochemical engineering processes and bioreactor applications.

SUMMARY OF THE INVENTION

The invention derives from the discovery that the macroscopic growth of multicellular aggregates, such as tumors, is modulated by solid stress (i.e., pressure exerted by solids, rather than fluids). Although solid stress inhibits the growth of such aggregates on a macroscopic level, continued cell proliferation and a decrease in apoptosis results in compaction of cells within the multicellular aggregate.

The invention thus features a method for controlling the growth of a multicellular aggregate in vitro. The method entails: (i) embedding a plurality of cells in a growth matrix, (ii) measuring the level of solid stress on the cells, (iii) modulating the level of solid stress on cells within the growth matrix, and allowing the cells to grow within the growth matrix, thereby forming a multicellular aggregate, and thereby controlling the growth of the multicellular aggregate in vitro.

The invention also provides a method for producing a multicellular aggregate having a pre-selected size; the method entails: embedding a plurality of cells in a growth matrix, and allowing the cells to grow within the matrix, wherein the growth matrix exerts a degree of solid stress on the cells adequate to achieve a multicellular aggregate of the pre-selected size. In a variation of the method, one can produce a multicellular aggregate having a pre-selected size and shape. Typically, this method is carried out by embedding a plurality of cells in a growth matrix, and allowing the cells to grow within the matrix, wherein the growth matrix is contained within a vessel (e.g., a vessel that is non-uniform in shape), and the growth matrix together with the vessel exert a degree of solid stress (e.g., non-isotropic stress) on the cells adequate to achieve a multicellular aggregate of the pre-selected size and shape. These methods can be used to produce artificial tissues such as livers, skin, muscle, bone, and various other organs.

The cells may be tumor cells (e.g., from muscle, liver, colon, or mammary tumors) or non-tumor cells, such as healthy, wild-type cells. The cells can be derived from an established cell line, or they can be primary cells. Examples of preferred cell types include, without limitation, liver cells, pancreatic cells, brain cells, skin cells, muscle cells, mammary cells, and bone cells.

A variety of growth matrices having differing mechanical strengths may be used in the invention. For example, the cells can be grown in a matrix containing agarose, for example at a concentration of 0.3% to 2.0% (w/v). Alternatively, the cells may be grown in a matrix containing collagen, with or without a glycosaminoglycan such as hyaluronic acid. In another variation of this method, the growth matrix may contain alginate. In addition to containing a compound for producing a growth matrix having stiffness (e.g., agarose), the growth matrix contains nutrients for growing the cells. For convenience, conventional cell culture media can be used to dissolve the matrix-forming compound (e.g., agarose) and provide nutrients to the cells.

As shown by the examples provided below, multicellular aggregates that are grown in a non-isotropic stress field preferentially grow in the direction of the least stress. Thus, the invention also provides a method for modulating the growth pattern of a multicellular aggregate. This method entails embedding a plurality of cells in a growth matrix in which solid stress exerted by the matrix is non-isotropic and thereby defines a template which modulates the growth pattern of the multicellular aggregate. By allowing the cells to grow within the matrix, a multicellular aggregate is formed, having a shape that is dictated by the non-isotropic stress field. Such a method therefore can be used to produce multicellular aggregates of virtually any desired shape (e.g., physiologically relevant shapes, such as those of organs, or portions thereof, or shapes convenient for grafting or implantation).

In a variation of the methods described above, the invention provides a method for identifying a therapeutic compound for treating a multicellular aggregate. As described below, compounds that decrease solid stress exerted by multicellular aggregates are expected to provide a beneficial therapeutic effect by inhibiting collapse of vascular and lymphatic vessels within the multicellular aggregate, thereby facilitating blood flow and delivery of therapeutics throughout aggregates, and facilitating lymphatic drainage of tumors. This method for identifying therapeutic compounds entails:

embedding a plurality of cells in a growth matrix,
allowing the cells to grow within the growth matrix, thereby forming a multicellular aggregate,
treating the multicellular aggregate with a test compound, and
measuring a decrease in the level of solid stress on the multicellular aggregate following treatment with the test compound, relative to the level of solid stress prior to treatment, as an indication that the test compound is a therapeutic compound for treating the multicellular aggregate (i.e., as a reliever of solid stress).

In related aspect, the invention provides a method for treating a multicellular aggregate in a mammal. In this method, a mammal (e.g., a human or a rodent, such as a mouse, in an animal model of a human disorder) is identified as being afflicted with a multicellular aggregate (e.g., a tumor), and solid stress exerted by the aggregate is relieved. Relief of solid stress can be accomplished, for example, by administering to the mammal an antibody that specifically binds an integrin, or an enzyme that dissolves the extracellular matrix (e.g., a collagenase, hyaluronidase, or protease). Alternatively, the extracellular matrix can be dissolved (and solid stress relieved) by topical treatment of the extracellular matrix with heat, ultrasound, microwaves, radiation, or the like.

By "solid stress" is meant pressure exerted on a solid by another solid, for example stress exerted on a multicellular aggregate by a growth matrix. Solid stress, therefore, is distinct from interstitial fluid pressure.

By "multicellular aggregate" is meant a plurality of connected cells (e.g., as in a mass of tissue). The cells of such an aggregate may be tumorigenic or non-tumorigenic. They need not be, but can be, homogenous. Included are primary cells, as well as cells of established cell lines. If desired, the cells may be wild-type, mutated (naturally or intentionally), or genetically engineered to produce a recombinant gene product (e.g., a secreted protein).

The invention offers several advantages. The level of solid stress imposed on cells can readily be modulated by embedding and growing the cells in a growth matrix of a defined stiffness (i.e., gel strength). By controlling stress exerted on the multicellular aggregate, one can control the proliferation and apoptotic rates of cells (e.g., tumor cells) within the aggregate. By applying stress in a non-isotropic manner on the growing multicellular aggregate, one can shape the multicellular aggregate into nearly any shape. Other features and advantages of the invention will be apparent from the following detailed description, and from the claims.

BRIEF DESCRIPTION OF THE DRAWINGS

FIGS. 4A and 4D depict cell proliferation, with dependence on spheroid diameter depicted in FIG. 4D. The range was 180–520 μm for 0.7% gel spheroids. The size distributions of the two samples were comparable. FIGS. 4B and 4E depict cell apoptosis, with FIG. 4E depicting dependence on spheroid diameter. The range was 180–520 μm for free suspension spheroids, 240–440 μm for 0.7% gel spheroids (comparable size distributions). FIG. 4C depicts cell density. The mean ± SE of the spheroid population is shown. Bold bars in FIGS. 4D and 4E schematically depict proliferation and apoptotic rates.

DETAILED DESCRIPTION

Figure 1:
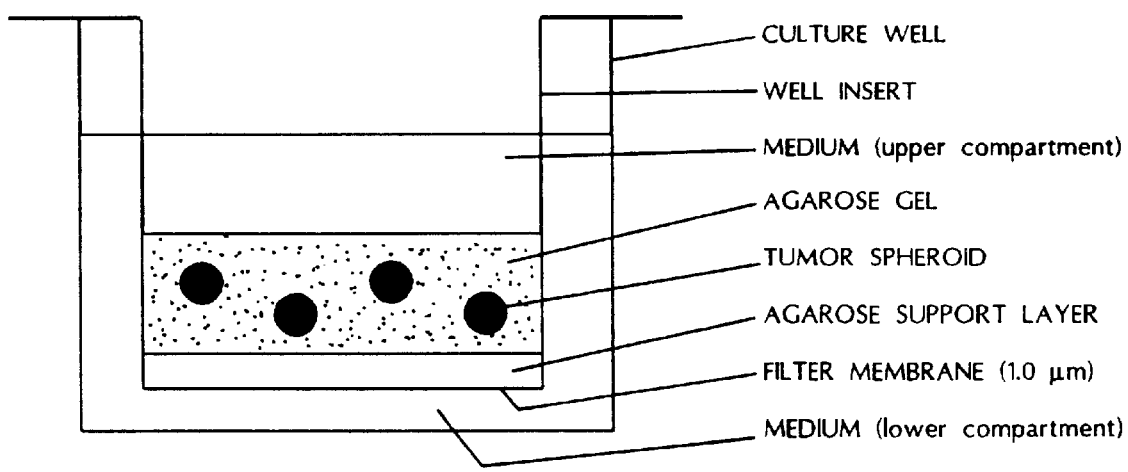
FIG. 1 is a schematic representation of an exemplary apparatus for growing multicellular aggregates in a growth matrix such as an agarose gel.

The invention derives from the discovery that solid stress exerted on a multicellular aggregate alters the growth pattern of the multicellular aggregate. More specifically, solid stress inhibits growth of the aggregate on a macroscopic level and decreases the apoptotic rate of cells within the aggregate, without affecting the cell proliferation rate. Consequently, solid stress causes compaction of cells within the aggregate. Thus, the invention provides in vitro methods for modulating the growth of multicellular aggregates which entail measuring the solid stress exerted by the multicellular aggregate (e.g., for identifying compounds that may relieve solid stress imposed upon vessels within tumors and enhance delivery of therapeutics to the aggregate).

As exemplified by the working examples that follow, the invention provides a method for controlling the growth of a multicellular aggregate in vitro. In this method, cells are embedded in a growth matrix, and allowed to grow within the matrix and thereby form a multicellular aggregate. Growth of the multicellular aggregate within the growth matrix is controlled by measuring and modulating the level of solid stress on the aggregate within the matrix.

The multicellular aggregate can be formed from any of a variety of cell types, with mammalian cells being preferred. Such cells can be primary cells, or they can be obtained from an established cell line. Numerous cell types are publicly available from sources such as the American Type Culture Collection, for example. In practicing the invention in vitro, cells typically are embedded in the growth matrix at a concentration of about 1,000 to 5,000 cells/ml, and allowed to form multicellular aggregates by maintaining the cells within the matrix for about 10 to 100 days (typically, 20–60 or 20–40 days). Conventional cell culture media can be used to provide nutrients to the cells, and the cell culture media typically is replaced daily.

A variety of growth matrices are suitable for use in the invention. Growth matrices such as agarose, alginate, collagen, and collagen supplemented with glycosaminoglycans, can readily be prepared by one of ordinary skill in the art. Typically, such growth matrices are prepared by dissolving the matrix-forming compound (e.g., agarose) in a conventional cell-culture medium known to be suitable for growing the cells of choice (e.g., Dulbecco's Modified Eagle's Medium). Agarose generally will be used at a concentration of 0.3 to 2.0% (w/v); concentrations of about 0.9% agarose or higher substantially inhibit growth of the multicellular aggregate. Alginate generally is used at a concentration of about 0.5% to 35% (typically, 0.5% to 4%), and collagen typically is used at a concentration of about 0.05% to 0.3% (e.g., 0.1% to 0.3%). If desired, collagen growth matrices can be supplemented with glycosaminoglycans (e.g., hyaluronic acid) typically at a concentration of about 0.1 μg/ml to 10 μg/ml.

When multicellular aggregates grow in in vitro growth matrices, such as agarose gels, stress gradually accumulates around the aggregate due to the progressive displacement of the matrix by the growing cellular mass. The pressure exerted by the stress field can be calculated based on the size of the growing aggregates and the mechanical properties of the growth matrix. A detailed description of an exemplary method for determining the level of stress exerted is provided below. Other methods for measuring solid stress also may be used. For example, the stress can be measured directly using optical methods, such as polarized light microscopy to assess the strain placed upon the growth matrix surrounding the multicellular aggregates.

By measuring and modulating the level of solid stress initially placed on cells that form a multicellular aggregate, one can control the growth of the aggregate within a growth matrix. The initial levels of solid stress can be increased by increasing the stiffness of the growth matrix (e.g., concentration of agarose). As described below, increasing the initial level of solid stress in a growth matrix inhibits the macroscopic growth of the multicellular aggregate and decreases the apoptotic rate of the cells within the aggregate, without affecting the proliferation rate. Thus, increasing the initial solid stress on the aggregate leads to compaction of cells within the aggregate.

The effects of solid stress on the growth patterns of multicellular aggregates can be reversed by alleviating the solid stress. For example, in vitro, aggregates can be released from growth matrices by dissolving the growth matrix. Agarose, for example, can be dissolved by treating the agarose gel with agarase at a concentration of 1 to 10 U/ml (typically, 5 U/ml) until the gel is dissolved (e.g., for 2 days). Growth matrices that contain collagen can be dissolved by treating the matrix with collagenase at a concentration of about 1 to 5% in PBS (e.g., 3%). Growth matrices containing alginate can be dissolved by changing the ionic strength of the matrix, e.g., by infusing manganese into the matrix. Once the extracellular matrix is dissolved, the released multicellular aggregates can be grown in culture medium as free suspensions.

In an in vivo setting (e.g., in a mammal afflicted with a tumor or a benign multicellular aggregate), solid stress exerted by the multicellular aggregate is sufficient to cause the collapse of blood and lymphatic vessels. The solid-stress-induced pressure on blood vessels, resulting in collapse of vessels, can inhibit delivery of therapeutic agents throughout the multicellular aggregate. Similarly, solid-stress-induced pressure on lymphatic vessels can impair lymphatic draining in cancer patients. Thus, compounds and methods for relieving solid stress are useful in therapeutic regimens for treating patients afflicted with tumors.

In vivo, solid stress imposed by multicellular aggregates (e.g., tumors) can be relieved by modulating the mechanical properties of the interstitial environment. For example, solid stress can be relieved by treating the mammal with an anti-integrin antibody, such as antibodies that specifically bind $\alpha$ and $\beta$ integrins. Such antibodies can be obtained commercially or produced according to art-known immunization methods. Solid stress also can be relieved by treating the mammal with collagenase and/or hyaluronidase to dissolve collagen and/or hyaluronic acid in the extracellular matrix surrounding the multicellular aggregate. Alternatively, proteases, such as metalloproteases, can be used to break up the extracellular matrix and relieve solid stress imposed on the multicellular aggregate.

Although such antibodies and enzymes can be delivered to the multicellular aggregate by systemic administration to the mammal systemically, these therapeutics typically will be administered topically or regionally to an area containing the multicellular aggregate. Generally, antibodies are administered at a dosage of 5 to 30 mg/kg of body weight, while enzymes are administered at a dosage of 1 to 10 mg/kg body weight. As an alternative to using antibodies or enzymes to alter the interstitial environment, non-biological means can be used. For example, solid stress can be relieved by dissolving the extracellular matrix surrounding the aggregate with heat, microwave radiation, ultrasound, and the like.

The in vitro methods described above can readily be adapted for identifying new compounds that relieve solid stress. In an exemplary method, cells (e.g., tumor cells) are embedded in a growth matrix, such as 0.3 to 1.0% agarose. The cells are allowed to grow until the resulting multicellular aggregates reach plateau phase (i.e., their final size), at which point the multicellular aggregate is treated with a test compound. Solid stress exerted by the multicellular aggregate is determined both before and after treatment with the test compound, and a decrease in the stress levels indicates that the compound is useful for treating the multicellular aggregate. Virtually any compound (e.g., polypeptides or small organic molecules) can be used as the test compound, provided it can diffuse through the growth matrix. In an alternative method, the cells are treated with the test compound prior to reaching plateau phase, or even before embedding the cells in the growth matrix.

Because growing multicellular aggregates are responsive to solid stress imposed by the growth matrix, the growth pattern of a multicellular aggregate can be modulated by growing the aggregate in a non-isotropic stress field. The multicellular aggregate preferentially grows in the direction of the least stress. In a growth matrix in which the stress field is essentially uniform, cells grow into spheroid multicellular aggregates. The stress field can be made non-isotropic (e.g., orthotropic) by containing the growth matrix within a rigid container, such as a glass tube, a cylindrical hollow fiber having porous walls for nutrient access, or a container of another desired shape. Solid stress exerted by the growth matrix, rather than the rigid container itself, constrains growth of the multicellular aggregate. By growing the cells in a growth matrix in a confined configuration and having a non-isotropic stress field, the non-isotropic stress field defines a template for growth of multicellular aggregate. As shown by the example provided below, the non-isotropic stress field exerted on the aggregate can be used to modulate the growth pattern of the aggregate and affect the final shape of the aggregate (e.g., to produce an ellipsoid, rather than spheroid, aggregate). By modulating the growth pattern of the multicellular aggregates, one can produce aggregates in a variety of physiologically relevant shapes (e.g., liver-shaped or pancreas-shaped aggregates as models of liver or pancreas). These shaped multicellular aggregates have many applications in tissue engineering, e.g., as implants or bioreactors.

EXAMPLES

Before describing the results of several working examples, various parameters of the methods employed, and of the invention in general, are described in detail. These examples are provided to illustrate, not limit, the invention, the metes and bounds of which are defined by the following claims.

METHODS

Culture of tumor spheroids in free suspension and agarose gels. The growth kinetics of three tumor cell lines were studied. Human colon adenocarcinoma cells (LS174T) were obtained from the American Type Culture Collection (ATCC; Rockville, Md.). Murine mammary carcinoma cells (MCaIV) were isolated from a spontaneous tumor (Department of Radiation Oncology, Massachusetts General Hospital, Boston, Mass.); other suitable murine mammary carcinoma cells are available from the ATCC. BA-HAN-1 rat rhabdomyosarcoma cells (clones A, B, C; from least to most differentiated) were provided by Drs. C.-D. Gerharz and H. Gabbert (Institute of Pathology, University of Dusseldorf, Germany). Other suitable rhabdomyosarcoma cells can be obtained from the ATCC or from commercial suppliers.

Cells were cultured in Dulbecco's Modified Eagle's Medium containing 3.7 g/l NaHCO$_3$, 10% fetal calf serum, 1% glutamine, and glucose (at 1.0 g/l for LS174T and MCaIV, and at 4.5 g/l for BA-HAN-1). Tumor cells were grown as multicellular spheroids in free suspension or in agarose gels of varying agarose concentrations (0.3% to 2.0%). The cells were grown in agarose gels in "well inserts" that were suspended between upper and lower compartments containing medium. Gels seeded with single-cell suspensions were prepared in 1-inch (outer diameter), sterile well inserts (Collaborative Biomedical Products, Bedford, Mass.) with porous, 1 $\mu$m filter membranes. This configuration resulted in two separate medium compartments, an upper one and a lower one (see FIG. 1).

Agarose (type VII, low gelling temperature) was obtained from Sigma (St. Louis, Mo.), and stock solutions of 2.0% (w/v) agarose dissolved in double-distilled water were prepared. Final agarose concentrations (ranging from 0.3% to 2.0%) were obtained by adding the appropriate amounts of double-strength medium (Gibco/BRL) and cell culture medium (described above) to the 2.0% agarose stock solution (Iscove et al., Academic Press, 1979, in Immunological Methods, pgs. 379–385). The bottom of each well insert was first coated with a supportive layer of 1% agarose (in a volume of approximately 0.5 ml), which was allowed to gel at room temperature for 10 minutes. The next layer of agarose was formed by adding a 2-ml liquid solution of agarose (at the appropriate concentration, as described above) inoculated with single tumor cells at a controlled cell seeding density. The pH of the liquid agarose was 7.3±0.1. During the inoculation process, the cell suspension was added at a time when the agarose solution was still liquid (>37° C.), yet cool enough to prevent cell damage (<40° C.). The cell-containing agarose medium was then allowed to gel at room temperature for 20 minutes. Finally, 3 ml of culture medium were added to the upper and lower compartments. The medium in each compartment was changed daily, and the spheroid cultures remained viable for at least 60 days.

Spheroids of cells grown in free suspension served as controls. The plastic surface of the lower compartment was first coated with a thin film of 1.0% agarose to prevent cell attachment. A single-cell suspension mixed with 3 ml culture medium was then introduced into the lower compartment. The initial cell seeding density matched the one used for the cultures grown in agarose gels. For the controls, the well insert was filled with a cell-free 1.0% agarose gel. Culture medium (3 ml) was then added to the upper compartment. The culture medium in the upper compartment, but not the lower compartment, was changed daily. With this configuration, the nutrients for feeding the cells must travel through the cell-free agarose gel before reaching the cells in the bottom compartment. Thus, the free suspension spheroids faced a less favorable nutrient environment that did the cells embedded in agarose.

In selected experiments, tumor spheroids grown in agarose gels were released from the gel by enzymatic digestion of the agarose gel with 5 U/ml agarase (Sigma). The conditioned culture medium was collected from the lower and upper compartments prior to treatment of the gel with agarase, and the released spheroids were cultured in the conditioned medium for 72 hours. Subsequent culturing in free suspension was carried out as described above. As controls, free cell suspension controls were also treated with 5 U/ml agarase, to confirm that the agarase used to dissolve the agarose gels had no significant effect on spheroid growth.

To investigate the effect of a non-isotropic stress field on tumor growth, cells were grown in 0.7% and 1.0% agarose gels embedded in glass capillary tubes (1-mm ID, 1-cm length, Vitro Dynamics, Rockaway, N.J.). Free suspension controls were grown in the central section (0.4 cm length) of capillary tubes, the extremities of which (0.3 cm on each side) were filled with cell-free, 1.0% agarose. All tubes were floated in a Petri dish containing 10 ml culture medium. The initial cell seeding density for the controls was the same as the density used for the isotropic stress experiments. After 25 days, the cell-containing gels were expelled from the glass tubes by pressure and resuspended in culture medium. Growth was monitored for 15 additional days.

Spheroid volumetric growth was assessed every 2 to 4 days (for up to 60 days) by measuring spheroid diameter using high-resolution videomicroscopy. At least 50 spheroids were measured at each time point in each well. Only spheroids that were more than two spheroid diameters apart from each other were considered to ensure that their stress fields did not overlap. Clonal efficiency was measured and defined as the ratio (expressed in %) of the number of spheroids (aggregates with >10 cells) present in the well at time t divided by the number of cells seeded at time t=0.

Mechanical properties of agarose gels and stress field computation. The growth process of tumor spheroids in agarose gels is characterized by an equilibrium between the thrust of growing tumor cells and the elastic constraint of the agarose chains. To be able to divide, cells (spheroids) must stretch the polymer network (i.e., matrix) surrounding the cells; cells cannot digest the matrix or migrate through it. The network, in turn, exerts an elastic stress on the spheroid surface. As growth proceeds, an elastic stress field builds around the spheroid, the magnitude of which depends on the mechanical properties of the agarose gel. In addition, during growth, fluid will be squeezed out from the gel regions proximal to the spheroid surface, leading to compaction of the gel around the spheroids. Therefore, to calculate the stress around a spheroid growing in a gel, one defines a constitutive equation of the gel, which relates the strain to the stress, and determines the mechanical parameters with appropriately designed experiments. The agarose gel is assumed to be a poroelastic material, i.e., a hyperplastic polymer network filled with a fluid. Thus, the gel can be described with an exponential-hyperbolic strain energy function with four constitutive parameters $$\left( W = C\left(e^{\beta(I-3)} - 1\right) + \gamma \frac{(III-1)}{(III-\phi_0)^n} \right)$$

where I and III are the first and third strain invariants, and C, $\beta$, $\gamma$ and n are empirical parameters. The chosen strain energy function adequately described the traction and compression states of agarose gels, as determined in confined and unconfined compression tests. In these tests, a fixed quantity of agarose was cast in a stainless steel container of 38 mm diameter and gelled at 4° C. for 1 hour. The system was then transferred to a dynamometer (Inston Machine Mod. 4204) to determine the constitutive relation between stretch and applied load. For confined compression tests, the agarose sample was kept in the metallic mold to prevent radial displacement. The sample was compressed by the upper surface with a porous stainless steel disc (37.5 mm in diameter) directly connected to the load cell. For unconfined compression test, the agarose sample was removed from the metallic mold and compressed by a non-porous disc. A cross-head speed of 0.06 mm/min was used to obtain quasi-static tests. All tests were performed at a controlled temperature of 37° C. The mechanical parameters (C, $\beta$, $\gamma$ and n) of agarose gels at 0.5, 0.7, 0.8, 0.9 and 1% were then obtained by fitting the experimental data. The stress field around the spheroid was calculated by integrating the equilibrium equations, assuming that the spheroids were not interacting mechanically, i.e., the stress field around a given spheroid did not overlap with that of a neighboring spheroid. The local gel concentration around the growing spheroid also was calculated.

Proliferation and apoptosis assays. A monoclonal antibody specific the proliferating cell nuclear antigen (PCNA), TDT-mediated dUTP-biotin nick end-labeling (TUNEL), and propidium iodide assays (PI) were used to quantify proliferating cells, apoptotic cells, and total cell number, respectively, in frozen sections of tumor spheroids. Spheroids were isolated manually, directly (from free suspensions) or after partial digestion (using 5 U/ml agarase) of the agarose gel. The spheroids then were frozen in OCT medium in a dry ice/methanol bath. Using a cryostat, thin sections (8 to 10 $\mu$m) of the spheroids were cut. The thin sections, on slides, were fixed for 30 minutes in 0.2% paraformaldehyde, followed by 10 minutes in 100% ethanol, then rinsed three times in phosphate-buffered saline (PBS). Slides were then used either for the PCNA or the TUNEL assay. PCNA sections were incubated for 60 minutes with monoclonal mouse anti-PCNA (DAKO, Santa Barbara, Calif.; diluted 1:50 in PBS containing 0.5% BSA), then for 30 minutes with streptavidin-conjugated FITC (BioSource International, Camarillo, Calif.; 1:50 in PBS containing 0.5% BSA). Each step was followed by a three-step wash in PBS. Apoptosis was measured using the MEBSTAIN apoptosis kit, which employs the TUNEL assay (#8440, MBL, Nagoya, Japan). To determine the total cell number, all slides were incubated for 30 minutes with 1 mg/ml PI (Sigma), rinsed three times in PBS, and mounted in PBS-glycerol. Sections ere imaged using an epi-fluorescence microscope (Zeiss Axioplan, Oberkochen, Germany) and high-resolution digital imaging. The percentage of proliferating cells was obtained by dividing the number of PCNA-positive cells by the total number of cells (PI-stained cells). A similar procedure was used to determine the percentage of apoptotic cells.

The results of several experiments, carried out as examples, now follow.

Example I
Solid Stress Inhibits Tumor Spheroid Growth

This example demonstrates that the growth kinetics of multicellular aggregates are modulated by solid stress. The initial stiffness of the growth matrix accelerates the response to growth-induced stress. To demonstrate the effects of solid stress on growth, tumor spheroids were cultured in gels of increasing agarose concentrations (as described above), thereby increasing the initial stiffness of the growth matrix in which the cells were embedded. As described below, solid stress inhibited tumor growth of cells from each of the species tested (human, mouse, and rat), tissues of tumor origin (colon, mammary, and muscle), and differentiation state (claims A, B, and C, of the BA-HAN-1 cell line). While the examples set forth below utilized agarose gels, similar results were obtained when a collagen gel was used (at 2.5 mg/ml).

Figure 2A:
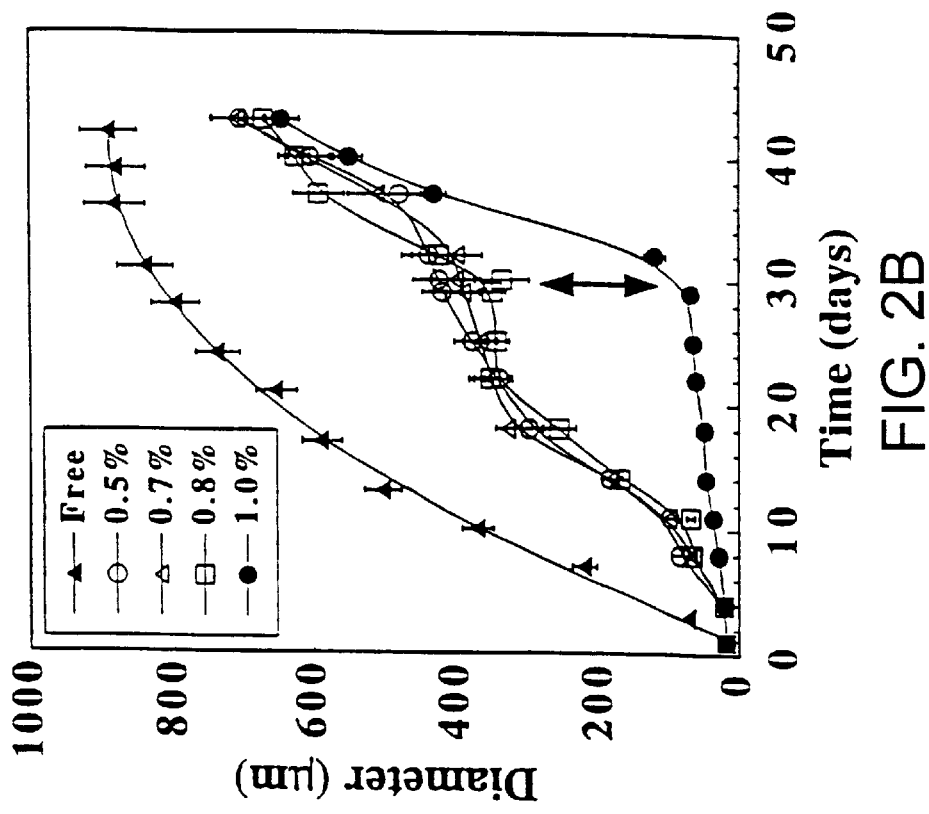
FIG. 2A is a graph depicting the growth kinetics of LS174T spheroids in free suspension and in 0.3, 0.5, 0.7, 0.8, 0.9 and 1.0% agarose gels. The mean diameter ± the standard error (SE) of the spheroid population is shown for 5 separate experiments (with 50 to 80 spheroids at each time point for each culture condition).
Figure 2B:
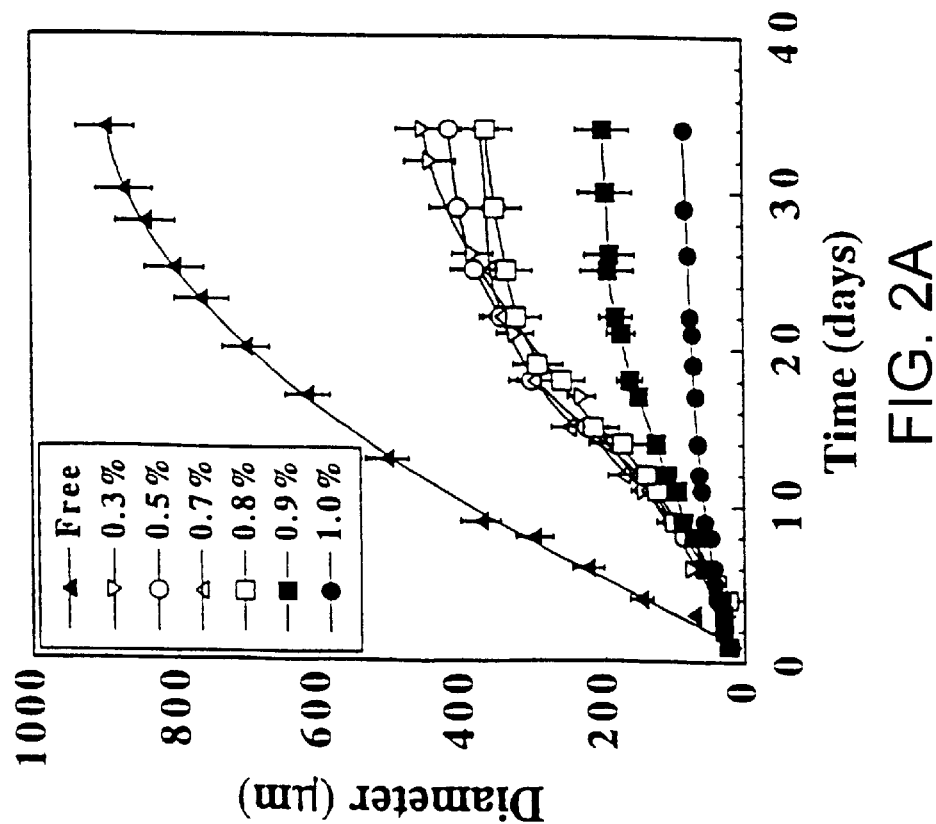
FIG. 2B is a graph depicting the growth kinetics before and after (arrow) release of spheroids from the gel (from 0.5, 0.7 and 1.0% agarose). The mean diameter ± SE of the spheroid population is shown; the results are representative of 5 separate experiments.

Human Colon Adenocarcinomas: For spheroids of human colon adenocarcinoma cells (LS174T cells), similar growth rates and final spheroid sizes were obtained at gel concentrations of 0.3, 0.5, 0.7, and 0.8% agarose. The mean diameter ± the standard error (SE) was 363±37.2 to 450±37.9 $\mu$m. The diameters obtained by growing the cells in spheroids were significantly lower than the diameters obtained by growing cells as free suspensions (897±40.0 $\mu$m, p<0.001), indicating the low levels of agarose in the growth matrix significantly inhibit cell growth. At higher agarose concentrations of 0.9% and 1.0%, growth of the tumor spheroids was further inhibited, with mean diameters of 200±37.7 and 85±9.3 $\mu$m, respectively (FIGS. 2A–2B). These data indicate that a threshold for significant growth inhibition is reached at an agarose concentration of 0.9% to 1.0% (FIGS. 2A–2B).

Although the growth kinetics varied among the culture conditions, the clonal efficiencies (i.e., a measure of spheroid formation, as described above) were similar (>90%) at all of the culture conditions (i.e., for free cell suspensions or at agarose concentrations ranging from 0.3% to 1.0%). Clonal efficiencies were significantly reduced only at higher agarose concentrations. For example, at 1.4% agarose, the clonal efficiency was reduced to 12%, and at 1.8% agarose, the clonal efficiency was reduced to 5%.

Rat Rhabdomyosarcomas: While the results described above were obtained with human colon adenocarcinoma cells, similar results also were obtained with three rat rhabdomyosarcoma clones. Three BA-HAN-1 rat rhabdomyosarcoma clones, at varying states of differentiation, were used. The resulting spheroids of the three clones displayed similar growth rates and final sizes when cultured in 0.7, 0.8, 0.9, and 1.0% gels. The spheroid diameters ranged from 218±16.6 to 273±18.3 $\mu$m, which was significantly smaller than the diameters produced with the same cells in free suspension (1050±87.0 $\mu$m; p<0.002). For all of the culture conditions, the clonal efficiency was greater than 90%. At a higher agarose concentration (1.4%), rhabdomyosarcoma spheroid growth was further reduced (102±10.7 $\mu$m) and the clonal efficiency was decreased to 20%. Thus, solid stress inhibits growth of rhabdomyosarcoma spheroids.

Murine mammary carcinomas: An inhibition of tumor growth also was observed with MCaIV murine mammary carcinoma spheroids. At agarose gel concentrations of 0.3, 0.5, and 0.7%, the mean diameter of the murine mammary tumor spheroids ranged from 135±1.40 to 141±19.8 $\mu$m. At a higher agarose concentration (1.0%), tumor growth was significantly inhibited; the mean diameter was 55±10; p<0.002. At all of the agarose concentrations (0.3 to 1.0%), the clonal efficiency was greater than 87%.

Threshold Levels of Solid Stress: As shown herein, the growth of tumor spheroids in gels is responsive to a threshold level of stress, with the stress accumulating locally due to a gradual displacement of the gel by the growing spheroids. Although the final size of spheroids is dependent upon the initial stiffness of the growth matrix (e.g., agarose concentration), solid stress accumulates around spheroids to a threshold level that is comparable for all spheroids which have reached their final size (i.e., plateau phase), regardless of initial stiffness of the growth matrix. In other words, the multicellular aggregates grow in the growth matrix until a threshold (i.e., growth-inhibitory) level of solid stress is reached. As shown in Table 1, the cells in the multicellular aggregates reach a threshold level of solid stress of approximately 45 to 120 mm Hg. The calculations of accumulated stress also showed that the stress field surrounding a plateau-phase spheroid drops to its initial, pre-growth value within a distance of one spheroid radius. In other words, the calculations of stress fields in the gel are not due to spheroids within the gel exerting stress on each other, since spheroids that were closer than one diameter apart ere excluded from the calculations.

TABLE 1

Solid stress calculations around spheroids cultured in gels of varying initial concentrations of agarose. Spheroid size refers to the average size of the population of spheroids. The interfacial gel concentration is the effective gel concentration faced by an average-sized spheroid in its growth plateau phase.

| Gel concentration | Initial spheroid size [μm] | Final spheroid size [μm] (from FIG. 2A) | Final Stress around spheroid [mm Hg] |
|---|---|---|---|
| 0.5% | 20 | 414 | 45 |
| 0.7% | 24 | 370 | 105 |
| 0.8% | 24 | 360 | 100 |
| 0.9% | 23 | 200 | 120 |
| 1.0% | 24 | 85 | 50 |

Example II
Tumor Spheroid Growth Resumes Following Stress Alleviation

To provide further evidence that solid stress modulates growth of multicellular aggregates, stress was alleviated, and the effects of stress alleviation were ascertained. In this experiment, human colon adenocarcinoma cells (LS174T cells) were grown to plateau phase spheroids in agarose gels. To alleviate the stress placed on the spheroids, the agarose gels were enzymatically digested with agarase, as described above. The released tumor spheroids then were placed in an equivalent volume of "used" cell culture medium for an additional 72 hours and grown as free suspensions. As shown in FIG. 2B, the spheroids resumed growth within 2 to 4 days. The growth rates of spheroids released from agarose gels were comparable to those obtained for control cells in free suspension. The diameters of the released spheroids increased until they eventually were comparable to those obtained for spheroids that had been grown as free suspensions. Similar results were obtained or BA-HAN-1 rat rhabdomyosarcoma spheroids released from gels. Thus, this example shows that the inhibitory effect of stress on growth is reversible, and relaxation of stress allows growth-inhibited spheroids to resume normal growth kinetics.

Example III
Use of Non-uniform Stress to Modulate the Shape of Growing Multicellular Aggregates This example demonstrates that the shape of a growing multicellular aggregate can be controlled by modulating the stress field in which the aggregate grows. More specifically, multicellular aggregates preferentially grow in the direction of least stress. In this example, LS174T cells were grown in cylindrical glass capillary tubes with an inner diameter comparable to the final size of free suspension spheroids (1 mm). With this configuration, radial stress on the growing spheroid increases faster than does axial stress, thereby resulting in a non-isotropic stress field.

Figure 3A:
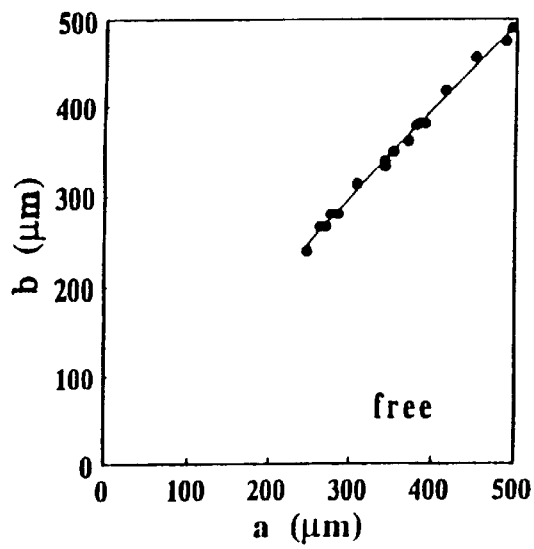
FIGS. 3A–3C are graphs depicting the growth of LS174T in free suspension and gels confined in 1.0-mm ID glass capillary tubes (orthotopic stress experiments). The longitudinal (b) versus radial dimensions (a) of tumor aggregates are shown for spheroids in free suspension after 25-day culture in glass tubes (FIG. 3A, fit: y=0.99x+0.70, $r^2$=0.99); in 0.7% gels after 25 days (FIG. 3B, fit: y=2.23x−43.5, $r^2$=0.86) ; or in 0.7% gels, 15 days after releasing the gels from the tubes (FIG. 3C, fit: y=1.05x+55.3, $r^2$=0.88). Dotted lines indicate y=x axis. Results are representative of three separate experiments, with 6 tubes per experiment for each condition.
Figure 3B:
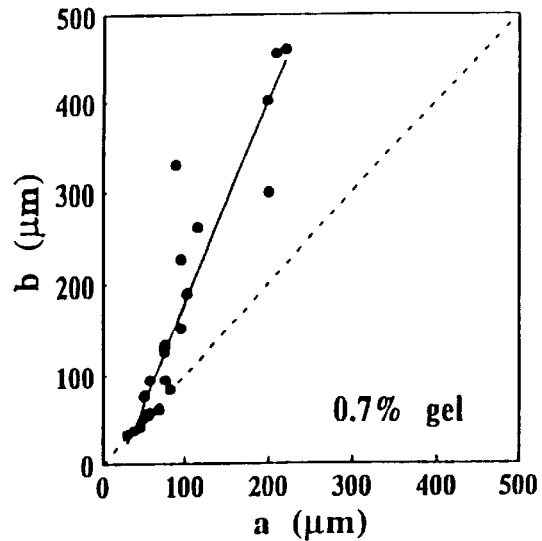
Figure 3C:
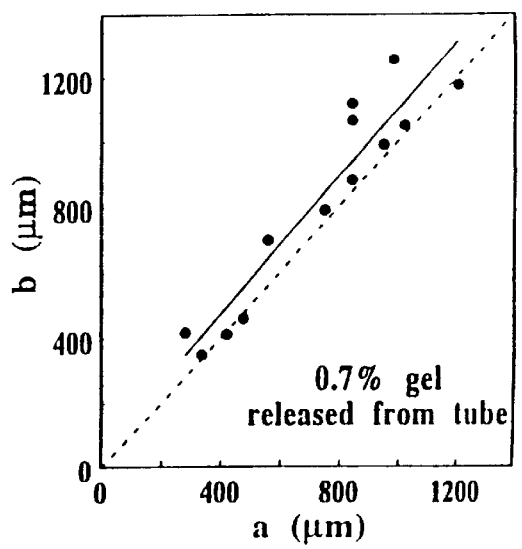

The growth patterns of cells in this confined geometry and in free suspension were compared with cells in this confined geometry and in 0.7% agarose gels (FIGS. 3A–3C). To characterize the shapes of the resulting multicellular aggregates, the following calculations were used. For each culture condition, the dimension of the aggregate along the tubes's longitudinal axis (b) versus the dimension along the tubes's radial axis (a) was plotted, as shown in FIGS. 3A–3C. At 25 days after seeding the cells in the tubes, cells in free suspension grew to nearly perfect spheroids, as indicated by a slope (b/a) of 0.99 (FIG. 3A; $r^2=0.99$). By contrast, the multicellular aggregates in the 0.7% agarose gels grew to ellipsoid shapes, with the longer axis parallel to the longitudinal axis of the capillary tube. This difference in the shape of cells grown in agarose can be appreciated quantitatively, as the slope (b/a) for these cells was 2.23 (FIG. 3B; $r^2=0.86$). To confirm that the differences in shape were due to the solid stress exerted upon the multicellular aggregates, the tumor aggregates were released by treating the gels with agarase (as described above). Upon release, the aggregates continued to grow into nearly spheroid shapes; at 15 days after release, the aggregates had a slope (b/a) of 1.05 (FIG. 3C; $r^2=0.88$). Similar results also were obtained after growing cells in 1.0% agarose gels. Thus, this example demonstrates that the growth pattern of multicellular aggregates can be modulated by growing cells in a non-isotropic stress field, with the cell aggregates preferentially growing in the direction of the least stress.

Example IV
Solid Stress Inhibits Cell Growth Without Inhibiting Cell Proliferation Rates The stress-dependent control of tumor growth, seen at the macroscopic level, is sensed at the microscopic levels by stress-induced changes in cellular growth patterns. While the size of a multicellular aggregate is influenced by solid stress, the proliferation rate of cells within the aggregate is not affected by solid stress. Thus, the solid stress exerted upon a multicellular aggregate results in compaction of cells within the aggregate. Two approaches were taken to elucidate the effects of solid stress on cell proliferation rates:

The growth kinetics of spheroids generally follow Gompertz law, an empirical relationship for volume growth $$\ln\left(\ln\frac{V}{V_0}\right) = -\alpha t + \frac{V_{max}}{V_0}$$

where V is a measure of spheroid size, $V_0$ is the initial size, and $V_{max}$ is the final spheroid size. Parameter a is the proliferation rate of cells in the proliferative pool when one uses a simple, two-compartment model (proliferating vs. non-proliferating cells). In the first approach, the growth curves for the spheroids, as shown in FIGS. 1A–1B, were re-plotted as ln (ln (V/$V_0$)) vs. time t. The data were best approximated by single linear fits ($r^2 \geq 0.93$), yielding values of parameter α, which is the cell proliferation rate. For LS174T spheroids, values of a were nearly identical for cells grown as free suspensions, or in 0.3–1.0% agarose gels. The value of α (i.e., the proliferation rate) did not change significantly after releasing the spheroids from the gels, even though an increase in tumor growth is seen on a macroscopic level after releasing spheroids from agarose gels (as described above). Similar results were obtained with spheroids formed by BA-HAN-1 rat rhabdomyosarcoma cells and MCaIV murine mammary tumor cells. This example thus indicates that, although solid stress inhibits the growth of the multicellular aggregates on the macroscopic level, the proliferation rate is not affected by solid stress.

Figure 4A:
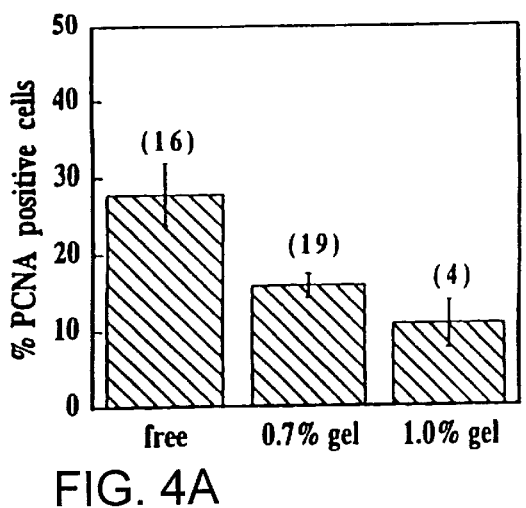
FIGS. 4A–E are histograms depicting the cellular characteristics of 28-day-old spheroids.
Figure 4B:
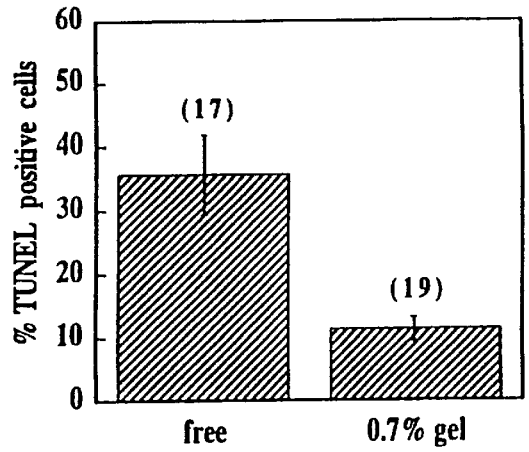
Figure 4C:
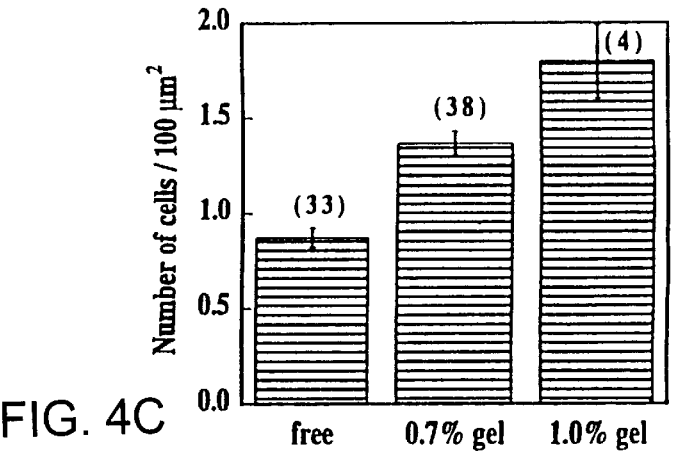

In a second approach, PCNA and TUNEL assays were used to quantify cell proliferation and apoptosis, respectively, in plateau-phase spheroids of LS174T cells. The cells were cultured either as free suspensions or in 0.7% or 1.0% agarose gels. With increasing gel concentrations (i.e., with increasing levels of solid stress), the percentage of proliferating and apoptopic cells decreased, and cellular density increased (FIGS. 4A–4C). Positive PCNA staining was limited to the outermost layers of cells in the multicellular aggregates, while apoptosis was detected exclusively in the central parts. The inner regions of spheroids grown as free suspensions contained large voids that were attributed to necrosis. Few of these types of voids were seen in spheroids grown in gels.

Figure 4D:
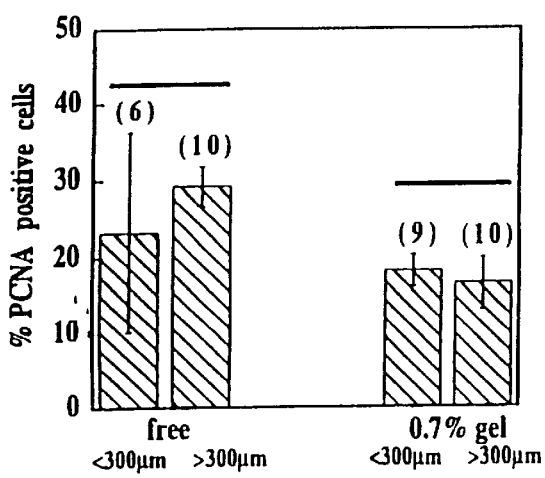

In analyzing the PCNA and TUNEL data, the data were divided into two categories, based on the size of the spheroid: small spheroids (having a diameter <300 $\mu$m) versus large spheroids (having a diameter >300 $\mu$m). For cells grown as free suspensions or in 0.7% gels, there was no significant correlation between the size of the spheroid and the number of proliferating cells measured with PCNA, as shown in FIG. 4D (linear curve fit: $r^2$=0.02 and 0.05, respectively). Thus, the proliferation rate is not significantly affected by solid stress.

Figure 4E:
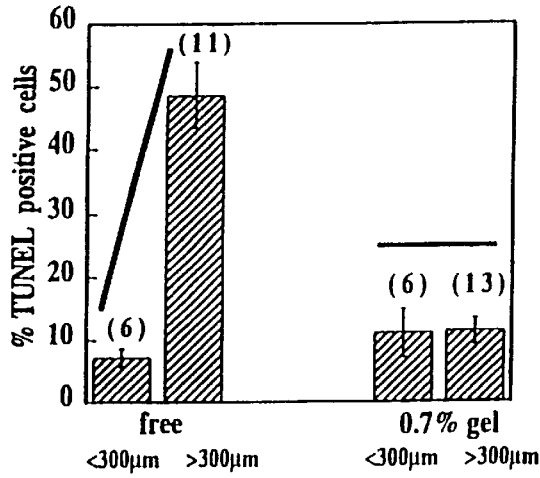

Although solid stress does not significantly affect cell proliferation rates, stress decreases the apoptotic rate. In spheroids in free suspensions, the percentage of apoptotic cells increased with an increase in spheroid size (FIG. 4E; $r^2$=0.72). In contrast, the percentage of apoptotic cells was not increased with size in cells grown in 0.7% agarose (FIGS. 4D–4E).

The data presented in this example show that, while accumulation of solid stress does not significantly affect the proliferation rate of cells in multicellular aggregates, accumulation of solid stress decreases the apoptotic rate of cells in multicellular aggregates. Consequently, one can infer that the growth of multicellular aggregates under solid stress is accompanied by compaction of cells within he aggregate.

Therapeutic Applications

The experiments summarized above demonstrate that multicellular aggregates grow, macroscopically, until a threshold level of solid stress (approximately 45–120 mm Hg) is accumulated at the surface of the spheroid. Additional cell proliferation results in compaction of the cells within the multicellular aggregate. Consequently, such multicellular aggregates can exert as much as 45–120 mm Hg of solid stress in vivo. This amount of pressure is sufficient to induce a local collapse of blood vessels within tumors or other multicellular aggregates in vivo, since tumor microvascular pressures average only 6–17 mm Hg. Thus, solid pressure exerted by growing tumors is sufficient to restrict blood flow throughout tumors. Similarly, the high levels of pressure generated by tumor growth, as shown by the above experiments, are sufficient to induce the collapse of lymphatic vessels. Accordingly, the relief of solid stress within tumors or other multicellular aggregates can now be expected to increase blood flow and lymphatic drainage in such multicellular aggregates. In addition, the above examples show that increased levels of solid stress inhibit the rate at which cells in the multicellular aggregate undergo apoptosis. Thus, relief of solid stress in multicellular aggregates, such as tumors, now can be expected to increase the rate of apoptosis and thereby facilitate elimination of tumor cells or other undesirable cells of multicellular aggregates. Alleviation of solid stress can be accomplished by any of several suitable methods, as described above.

What is claimed is:

1. A method for controlling growth of a multicellular aggregate, the method comprising:
    providing a plurality of cells in a growth matrix or in a growth matrix in a vessel, wherein the growth matrix is a gel comprising agarose, alginate, or collagen,
    growing the cells in the growth matrix or in the growth matrix in the vessel to exert pressure on the cells,
    calculating a value representing pressure exerted on the cells by the growth matrix alone or by the growth matrix together with the vessel containing the growth matrix,
    modulating the level of pressure exerted on cells within the growth matrix or within the growth matrix together with the vessel containing the growth matrix, and
    continuing to grow the cells within the growth matrix or within the growth matrix in the vessel, thereby forming a multicellular aggregate,
    thereby controlling the growth of the multicellular aggregate.

2. The method of claim 1, wherein the multicellular aggregate comprises tumor cells.

3. The method of claim 1, wherein the multicellular aggregate comprises primary cells.

4. The method of claim 1, wherein the multicellular aggregate comprises cells selected from the group consisting of liver cells, pancreatic cells, brain cells, skin cells, bone cells, and muscle cells.

5. The method of claim 1, wherein the growth matrix comprises agarose.

6. The method of claim 1, wherein the concentration of agarose in the growth matrix is 0.3% to 2.0%.

7. The method of claim 1, wherein the growth matrix comprises collagen.

8. The method of claim 7, wherein the growth matrix further comprises a glycosaminoglycan.

9. The method of claim 1, wherein the growth matrix comprises alginate.

10. The method of claim 1, wherein the pressure exerted on the cells is non-isotropic.

11. The method of claim 10, wherein the growth matrix comprises agarose.

12. The method of claim 10, wherein the multicellular aggregate comprises tumor cells.

13. The method of claim 10, wherein the multicellular aggregate comprises primary cells.

14. The method of claim 10, wherein the multicellular aggregate comprises cells selected from the group consisting of liver cells, pancreatic cells, brain cells, skin cells, bone cells, and muscle cells.

15. The method of claim 1, wherein the cells are allowed to grow within the growth matrix in vitro.

16. The method of claim 5, wherein the cells are allowed to grow within the growth matrix in vitro.

17. The method of claim 10, wherein the growth matrix comprises alginate.

18. The method of claim 10, wherein the growth matrix comprises collagen.

19. The method of claim 10, wherein the growth matrix consists of agarose.

20. The method of claim 10, wherein the growth matrix consists of alginate.

21. The method of claim 10, wherein the growth matrix consists of collagen.

22. A method for producing a multicellular aggregate having a pre-selected size, the method comprising:
    embedding a plurality of cells in a growth matrix or in a growth matrix in a vessel, wherein the growth matrix is a gel comprising agarose, alginate, or collagen,
    growing the cells in the growth matrix or in the growth matrix in the vessel to exert pressure on the cells,
    calculating a value representing pressure exerted on the cells by the growth matrix alone or by the growth matrix together with the vessel containing the growth matrix, and continuing to grow the cells within the growth matrix or within the growth matrix in the vessel, wherein the growth matrix or the growth matrix together with the vessel exerts a degree of pressure on the cells adequate to achieve a multicellular aggregate of the pre-selected size.

23. The method of claim 22, wherein the multicellular aggregate is an artificial tissue.

24. The method of claim 22, wherein the pressure exerted on the cells is non-isotropic.

25. A method for producing a multicellular aggregate having a pre-selected size and shape, the method comprising:

embedding a plurality of cells in a growth matrix in a vessel, wherein the growth matrix is a gel comprising agarose, alginate, or collagen, growing the cells in the growth matrix in the vessel to exert pressure on the cells, calculating a value representing pressure exerted on the cells by the growth matrix together with the vessel containing the growth matrix, and continuing to grow the cells within the growth matrix contained within the vessel, wherein the growth matrix together with the vessel exerts a degree of pressure on the cells adequate to achieve a multicellular aggregate of the pre-selected size and shape.

26. The method of claim 25, wherein the multicellular aggregate is an artificial tissue.

27. The method of claim 25, wherein the pressure exerted on the cells is non-isotropic.

* * * * *